United States Patent [19]

Brown, Jr.

[11] 4,417,069

[45] Nov. 22, 1983

[54] METHOD OF PREPARING β-PHENYLETHYLCHLOROSILANES

[75] Inventor: Edgar D. Brown, Jr., Schenectady, N.Y.

[73] Assignee: General Electric Company, Waterford, N.Y.

[21] Appl. No.: 468,115

[22] Filed: Feb. 22, 1983

[51] Int. Cl.³ ............................................. C07F 7/08
[52] U.S. Cl. ................................................... 556/479
[58] Field of Search ........................................ 260/479

[56] References Cited

U.S. PATENT DOCUMENTS

| | | | |
|---|---|---|---|
| 2,954,390 | 9/1960 | Pike et al. | 556/479 |
| 3,057,902 | 10/1962 | Pike | 556/479 |
| 3,410,886 | 11/1968 | Joy | 556/479 |
| 3,567,755 | 3/1971 | Seyfried et al. | 556/479 X |
| 4,242,272 | 12/1980 | Koga et al. | 556/489 |

OTHER PUBLICATIONS

The Addition of Silicon Hydrides to Olefinic Double Bonds, Musolf and Speier, J. Org. Chem. 29, 2519 (1964).

*Primary Examiner*—Paul F. Shaver
*Attorney, Agent, or Firm*—Gary L. Loser

[57] ABSTRACT

There is provided a method for preparing β-phenylethylchlorosilanes comprising forming a mixture of styrene, a chlorosilane having at least one silicon-bonded hydrogen atom, a platinum catalyst and a tertiary amine, and heating the mixture in order to effect addition of the chlorosilane to styrene.

25 Claims, No Drawings

METHOD OF PREPARING β-PHENYLETHYLCHLOROSILANES

BACKGROUND OF THE INVENTION

The present invention relates to a novel process for the preparation of β-phenylethylchlorosilanes. More particularly, this invention is directed to the controlled addition reaction of a chlorosilane which contains at least one hydrogen atom bonded to silicon to styrene to produce a β-phenylethylchlorosilane.

The addition of silanes containing at least one hydrogen atom bonded to silicon to unsaturated organic compounds in general, and styrene in particular, is known in the art. Generally, such addition results in a mixture of various isomers. For example, in the addition reaction of methyldichlorosilane to styrene using a platinum catalyst, some of the silicon-bonded hydrogen atoms of the silane molecules attach to the carbon atom nearest the benzene ring while the silyl radicals of the silane molecules attach to the carbon atom farthest from the benzene ring, and some of the silicon-bonded hydrogen atoms and silyl radicals attach in the opposite positions. Accordingly, there results from such addition reaction a mixture of β-phenylethylmethyldichlorosilane and α-phenylethylmethyldichlorosilane. These reactions may be represented by the following equations respectively:

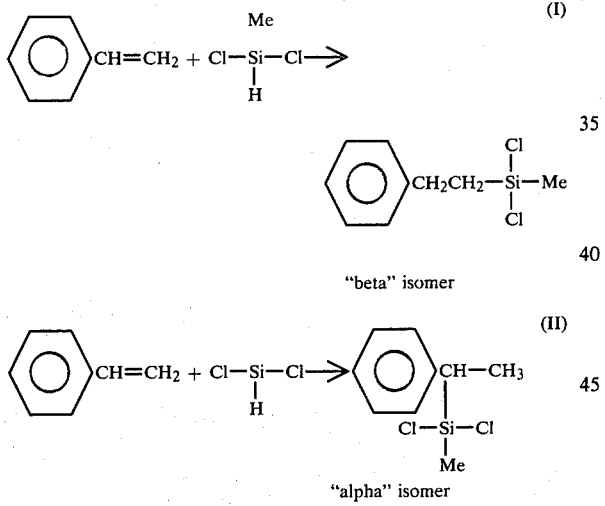

In the normal course of the addition reaction of a chlorosilane having at least one silicon-bonded hydrogen atom with styrene in the presence of a platinum catalyst, there is produced a mixture containing approximately 60 percent β-phenylethylchlorosilane and approximately 40 percent α-phenylethylchlorosilane. The ratio of beta isomer to alpha isomer remains at approximately 60:40 regardless of whether a monochlorislane, dichlorosilane or trichlorosilane is utilized as the adduct.

Inasmuch as alpha isomers are usually unstable, the general tendency has been to avoid them. Wagner et al. reported, Ind. Eng. Chem. 45,367 (1953), the use of a platinum-on-charcoal catalyst to obtain an increased amount of beta isomer when reacting trichlorosilane and styrene at 200° C. and under pressure for 20 hours. However, the use of platinum-on-charcoal catalyst to obtain a β-phenylethylchlorosilane is accompanied by certain disadvantages. Thus, for example, where a platinum-on-charcoal catalyst is employed, the reaction tends to exhibit long inhibition periods before starting. Moreover, the mixing of large amounts of reactants to overcome such inhibition period is usually accompanied by extremely exothermic and violent reactions upon initiation. Additionally, the use of platinum-on-charcoal catalyst, as suggested by Wagner et al., results in the polymerization of substantial amounts of styrene with a corresponding decrease in yield of the desired addition product unless special precautions such as temperature control and/or large excesses of chlorosilane are employed.

Musolf and Speier reported, J. Org. Chem. 29,2519 (1964), that the addition of certain silicon hydrides to phenylalkenes of the formula:

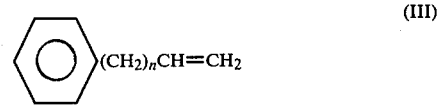

or

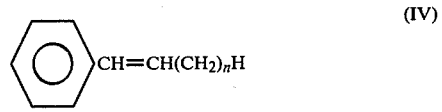

where n equals 0 to 4 and with chloroplatinic acid as the catalyst leads in each case to two products:

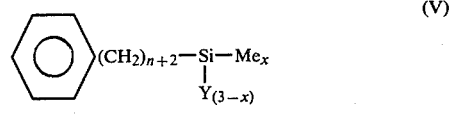

and

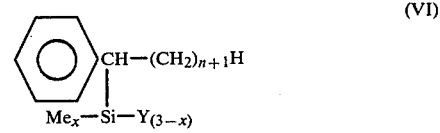

In their research Musolf and Speier studied examples with Y being equal to chlorine, fluorine or Me₃SiO and x equal to 0,1,2 and 3. The relative amounts of V to VI produced depended upon the nature of Y and the values of x and n. Substituents on the phenyl group in styrene also influenced the ratio of products of type V to products of type VI.

Pike and Borchert, U.S. Pat. No. 2,954,390, disclose that chlorosilanes having at least one silicon-bonded hydrogen atom can be added to styrene in the presence of tetrahydrofuran as solvent and platinum as a catalyst to provide the β-phenylethylchlorosilane isomer exclusively. It is further disclosed that the reaction involving the addition of a chlorosilane having at least one silicon-bonded hydrogen atom to styrene can be controlled to produce substantially higher proportional yields of β-phenylethylchlorosilanes over α-phenylethylchlorosilanes by conducting the reaction in the presence of a platinum catalyst and a highly polar organic ether solvent. Pike and Borchert suggest that the relative amount of beta isomer obtained is related to the polarity of the ether employed as solvent and to the ease with which the ether solvates the silicon atom of the silane employed in the reaction.

Koga et al., U.S. Pat. No. 4,242,272, disclose a method of producing an alkylphenylethyldichlorosilane comprising reacting a monoalkyldichlorosilane represented by the general formula $RHSiCl_2$, wherein R is an alkyl radical of 3 to 20 carbon atoms, and styrene in the presence of a complex of platinum-phosphine compound at a temperature of 30° C. to 200° C., preferably 30° C., to 110° C. A reaction time of 1 to 60 hours is normally employed.

The principal object of the present invention is to provide an improved process for preparing $\beta$-phenylethylchlorosilanes.

It is also an object of the present invention to provide a new and improved method of preparing $\beta$-phenylethylchlorosilanes by addition of a chlorosilane having at least one silicon-bonded hydrogen atom to styrene in the presence of a platinum-type catalyst and a tertiary amine position-directing agent, whereby extremely exothermic and violent reactions are avoided and whereby large amounts of solvent are not required to effect formation of the beta isomer.

Other objects and advantages of the present invention will become obvious from the following detailed description.

SUMMARY OF THE INVENTION

The present invention provides a method for preparing $\beta$-phenylethylchlorosilanes comprising forming a mixture of styrene, a chlorosilane having at least one hydrogen atom bonded to silicon, a platinum metal or platinum metal complex catalyst and an amount of tertiary amine effective for causing formation of $\beta$-phenylethylchlorosilane isomer, and heating the mixture in order to effect addition of the chlorosilane to styrene.

DESCRIPTION OF THE INVENTION

In accordance with the present invention there is provided a method for preparing $\beta$-phenylethylchlorosilanes comprising forming a mixture of styrene, a chlorosilane having at least one hydrogen atom bonded to silicon, a platinum-type catalyst and an amount of tertiary amine effective for causing formation of the $\beta$-phenylethylchlorosilane isomer, and heating the mixture to effect addition of the chlorosilane to styrene.

The process of the instant invention may be practiced with any chlorosilane having at least one silicon-bonded hydrogen atom, i.e., monochlorosilanes, dichlorosilanes and trichlorosilanes. The unsatisfied valence bonds of the silicon atom, if any, may be satisfied by nearly any organic radical, for example, aliphatic radicals, aromatic radicals, aralkyl radicals or alkaryl radicals. Generally, the chlorosilane reactant can be represented by the general formula:

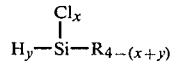

where R represents an alkyl radical such as methyl, ethyl, propyl and the like, an aryl radical such as phenyl, naphthyl and the like, an aralkyl radical such as benzyl, phenylethyl and the like, or an alkaryl radical such as methylphenyl, ethylphenyl, propylphenyl and the like, x has a value of from 1 to 3 inclusive, y has a value of from 1 to 3 inclusive and the sum of x and y equals 2 to 4 inclusive. Preferably, the chlorosilane utilized in practicing the present invention is trichlorosilane or methyldichlorosilane.

The ratio of chlorosilane to styrene can vary over a wide range; however, the mixture preferably contains no more than one molar excess of either reactant per mole of the other reactant. From a practical standpoint, particularly good results are obtained when the reaction mixture contains approximately equimolar amounts of chlorosilane and styrene. Excesses larger than one mole of either reactant per mole of the other reactant may be employed; however, no particular advantage is obtained thereby.

As a catalyst for the reaction of chlorosilane and styrene, any platinum-type catalyst can be used, for example, chloroplatinic acid, platinum-on-alumina or platinum-on-charcoal. Preferably, the catalyst is of the type described in U.S. Pat. No. 3,220,972, to Lamoreaux or U.S. Pat. Nos. 3,715,334 and 3,775,452 to Karstedt, all of which are incorporated by reference into the present disclosure. Ordinarily, about 5 ppm of catalyst calculated as platinum metal is necessary to initiate the reaction; however, the maximum amount of catalyst which can be utilized is limited primarily by cost considerations. It is believed that no more than about 50 ppm of platinum catalyst will be utilized, and preferably from 10 to 30 ppm of platinum catalyst will be included in the reaction mixture. In the most preferred embodiment of the instant invention about 20 ppm of a platinum metal or platinum metal complex catalyst is employed to initiate reaction.

An amount of tertiary amine is included in the reaction mixture as a position directing or beta-directing agent which increases the yield of $\beta$-phenylethylchlorosilanes. The tertiary amines employed in the practice of the present invention have the general formula:

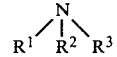

wherein $R^1$, $R^2$ and $R^3$ are selected, independently, from the group consisting of alkyl radicals, aryl radicals, aralkyl radicals and alkaryl radicals. $R^1$, $R^2$ and $R^3$ can be the same or different radicals. Preferably, $R^1$, $R^2$ and $R^3$ are alkyl radicals having from 1 to 8 carbon atoms and, most preferably, $R^1$, $R^2$ and $R^3$ are all butyl. Accordingly, the most preferred position-directing agent is tributyl amine.

Generally, the beta-directing tertiary amine is utilized in a ratio to platinum catalyst ranging from about 1:1 to about 3:1. Most preferably there is utilized about 2 parts tertiary amine per part platinum catalyst. Thus, in a preferred embodiment of the present invention there is included in the reaction mixture from 10 to 30 parts per million platinum and 10 to 90 parts per million tertiary amine. In a more preferred embodiment there is included in the reaction mixture 20 parts per million platinum and 20 to 60 parts per million tertiary amine. In the most preferred embodiment, the styrenechlorosilane reaction mixture includes 20 parts per million of a platinum metal or platinum metal complex catalyst (as Pt metal) and 40 parts per million of a tertiary amine, said tertiary amine most preferably being tributyl amine.

A 2:1 ratio of tertiary amine to platinum catalyst is preferred as under such condition 100% of the $\beta$- phenylethylchlorosilane isomer is produced and the reaction proceeds at a suitable rate without being extremely exothermic or violent. When the ratio of tertiary amine to platinum catalyst is much less than 2:1 the amount of beta isomer produced is less than 100 percent. Nevertheless, the yield of beta isomer is still substantially more than would be obtained without the presence of the beta-directing tertiary amine in the reaction mixture. On the other hand, when the ratio of tertiary amine to platinum catalyst is increased much beyond a 2:1 ratio, the reaction becomes somewhat sluggish.

In accordance with the present invention $\beta$-phenylethylchlorosilanes are produced by mixing styrene, a chlorosilane having at least one silicon-bonded hydrogen atom, a platinum catalyst and an effective amount of a tertiary amine position-directing agent, and heating the mixture to effect the desired addition of chlorosilane to styrene. If desired for ease of handling, the tertiary amine may be dissolved in styrene or other suitable medium before it is added to the reaction mixture, for example, on the order of about 1 percent. Using the preferred platinum/vinylsiloxane catalyst, the tributyl amine may be premixed therewith to form a stable position-directing catalyst.

The reaction of the present invention may be carried out either under pressure or at atmospheric conditions. Although the order of addition of the ingredients is not absolutely critical, it has been found that the highest yield of beta-isomer is obtained by first charging styrene to a suitable reactor. The desired amount of tertiary amine or solution of tertiary amine is then added to the reactor and the mixture stirred for 15 to 30 minutes. The total amount of platinum catalyst is next added to the reactor and the mixture is stirred for an additional 15 to 30 minutes. The reaction vessel containing catalyzed styrene is heated to about 80° C. and the addition of chlorosilane is begun. A cooling jacket may be utilized to aid in keeping the temperature of the reactor between 80° and 100° C. during addition of the chlorosilane. After all of the chlorosilane has been added to the reactor, heating of the mixture is continued for about one hour. After an hour, the mixture may be sampled and analyzed, by gas chromatography for example, to determine whether the reaction is complete. If the reaction is complete, the product is stripped, preferably under vacuum and a nitrogen sparge, to about 100° C. until excess styrene has been removed. Of course, those skilled in the art could easily adapt such process so that the product is made continuously.

The $\beta$-phenylethylchlorosilanes prepared according to the instant invention are useful in preparing phenylethyl-modified dimethyl silicone oils and the like. However, $\beta$-phenylethyltrichlorosilane prepared by the present method is particularly useful in preparing silicone resins which impart ultraviolet light and weathering resistance as described in the patent application of George F. Roedel, attorney docket 60SI-730, filed concurrently herewith and assigned to the same assignee as the present invention. Briefly, the Roedel patent application discloses that $\beta$-phenylethyltrichlorosilane may be reacted with alkyltrichlorosilanes, said alkyl group having from 1 to about 12 carbon atoms, to form an intermediate composition which copolymerizes with alkyd resins much more rapidly than heretofore possible.

In order that those skilled in the art might be better able to practice the present invention, the following example is given by way of illustration and not by way of limitation.

EXAMPLE

A solution of 1 percent tributylamine was made in styrene and sufficient platinum catalyst added so that the ratio of tributylamine to platinum catalyst was about 2:1. An amount of styrene was charged to a clean, dry reactor. An amount of the above solution was added to the styrene so as to provide 20 ppm platinum. The mixture of styrene, platinum catalyst and tributyl amine was then stirred for 15 to 30 minutes to provide a homogenous mixture. After the reaction vessel was heated to 80° C., the reactor cooling unit was turned on and an equimolar amount of trichlorosilane was slowly added to the mixture. The rate of trichlorosilane addition was regulated so as to maintain the reactor temperature within the range of 80° C. to 100° C. Following addition of all the trichlorosilane, heating of the reaction mixture was continued for another hour. After the additional hour of heating, the reaction was found to be complete by G.C. analysis, that is, less than 1 percent of both trichlorosilane and styrene was found. The reaction product was stripped at 100° C. and 25 mm pressure under nitrogen sparge until all excess styrene was removed. This yielded $\beta$-phenylethyltrichlorosilane product having a boiling point of 225° to 228° C. (at atmospheric pressure), a density of 1.2425 (d20/4) and a refractive index of 1.521.

I claim:

1. A method for producing $\beta$-phenylethylchlorosilanes comprising forming a mixture of styrene, a chlorosilane having at least one hydrogen atom bonded to silicon, a platinum metal or platinum metal complex catalyst and an amount of tertiary amine effective for causing formation of $\beta$-phenylethylchlorosilane isomer, and heating the mixture in order to effect addition of the chlorosilane to styrene.

2. The method of claim 1 wherein the chlorosilane has the general formula:

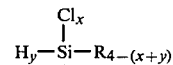

where R represents a radical selected from the group consisting of alkyl radicals, aryl radicals, aralkyl radicals and alkaryl radicals, x has a value of from 1 to 3 inclusive, y has a value of from 1 to 3 inclusive, and the sum of x and y equals 2 to 4 inclusive.

3. The method of claim 1 wherein the chlorosilane is trichlorosilane.

4. The method of claim 1 wherein the chlorosilane is methyldichlorosilane.

5. The method of claim 1 wherein there is no more than one molar excess of either reactant per mole of the other reactant.

6. The method of claim 1 wherein there are equimolar amounts of chlorosilane and styrene.

7. The method of claim 1 wherein the catalyst is selected from the group consisting of platinum metal, chloroplatinic acid, platinum-on-alumina and platinum-on-charcoal.

8. The method of claim 1 wherein the catalyst is a compound prepared by (A) forming a reaction mixture of (1) chloroplatinic acid with (2) at least two moles per gram atom of platinum of a member selected from the class consisting of (a) alcohols having the formula ROH, (b) ethers having the formula ROR, (c) aldehydes having the formula RCHO, and (d) mixtures thereof and (B) heating said reaction mixture at a temperature of from about 60° to 80° C. at a reduced pressure until the reaction product has a ratio of from about 2.0 to about 3.5 atoms of chlorine per atom of platinum, where R is a member selected from the class consisting of alkyl radicals containing at least 4 carbon atoms, alkyl radicals substituted with an aromatic hydrocarbon radical and alkyl radicals substituted with an OR¹ radical where R¹ is a member selected from the group consisting of monovalent hydrocarbon radicals free of aliphatic unsaturation and monovalent radicals free of aliphatic unsaturation and consisting of carbon, hydrogen and oxygen atoms with each oxygen atom being attached to two other atoms, one of which is a carbon atom and the other of which is a member selected from the class consisting of a carbon atom and a hydrogen atom.

9. The method of claim 1 wherein the catalyst is a compound prepared by contacting (A) a silicon material containing per molecule, at least one hydrogen atom attached to silicon, there being not more than two hydrogen atoms attached to any one silicon atom and (B) a material containing aliphatic carbon atoms linked by multiple bonds in the presence of a platinum-vinylsiloxane essentially free of chemically combined halogen and having at least 0.01 percent by weight platinum of the formula:

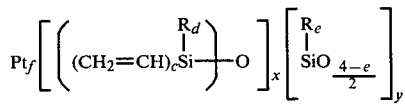

in which the ratio of the average gram atoms of halogen to gram atoms of platinum does not exceed 0.1, where R is selected from the group consisting of alkyl radicals, alkenyl radicals, cycloalkyl radicals, aryl radicals, aralkyl radicals and halogenated radicals of the aforementioned types, c is an integer equal to 1 to 3 inclusive, d is a whole number equal to 0 to 2 inclusive, e is a whole number equal to 0 to 3 inclusive, x is an integer equal to 1 to 100 inclusive, y is a whole number equal to 198 inclusive and the sum of x+y is equal to 1 to 199 inclusive and f has a value between about 0.67 to about 67, while f/x has a value up to about 0.67.

10. The method of claim 1 wherein the catalyst is a platinum-siloxane complex consisting essentially of chemically combined platinum and an organosiloxane of the average unit formula

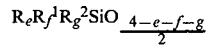

where R is free of aliphatic unsaturation and is selected from the group consisting of alkyl radicals, cycloalkyl radicals, and phenyl radicals; R¹ is selected from the group consisting of aliphatically unsaturated olefinic and acetylenic radicals; R² is selected from R¹ radicals chemically combined with platinum having an infrared absorption band at 7.5 to 7.6 and 8.3 microns in the spectrum of the platinum-siloxane complex, in which the available inorganic halogen which can be detected does not exceed that quantity which is sufficient to provide for an average ratio of gram atoms of halogen per gram atoms of platinum having a value greater than one and there is present at least three moles of R² units per gram atom of platinum, e has a value equal to 0 to 2 inclusive, f has a value equal to 0 to 2 inclusive, g has a value equal to 0.0002 to 3 inclusive and the sum of e, f and g has a value equal to 1 to 3.

11. The method of claim 1 wherein the amount of catalyst ranges from about 5 ppm to about 50 ppm calculated as platinum metal.

12. The method of claim 1 wherein the amount of catalyst ranges from about 10 ppm to about 30 ppm calculated as platinum metal.

13. The method of claim 1 wherein the amount of catalyst is about 20 ppm calculated as platinum metal.

14. The method of claim 1 wherein the tertiary amine has the general formula:

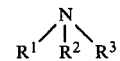

wherein R¹, R² and R³ are selected, independently, from the group consisting of alkyl radicals, aryl radicals, aralkyl radicals and alkaryl radicals and mixtures thereof.

15. The method of claim 14 wherein R¹, R² and R³ are alkyl radicals having from 1 to 8 carbon atoms.

16. The method of claim 1 wherein the tertiary amine is tributyl amine.

17. The method of claim 1 wherein the ratio of tertiary amine to catalyst as platinum metal ranges from about 1:1 to about 3:1.

18. The method of claim 1 wherein the ratio of tertiary amine to catalyst as platinum metal is about 2:1.

19. The method of claim 1 wherein there is present from about 10 to about 30 parts per million catalyst calculated as platinum metal and from about 10 to about 90 parts per million tertiary amine.

20. The method of claim 1 wherein there is present about 20 parts per million catalyst calculated as platinum metal and from about 20 to about 60 parts per million tertiary amine.

21. The method of claim 1 wherein there is present about 20 parts per million catalyst calculated as platinum metal and about 40 parts per million tributylamine.

22. A method for producing β-phenylethylchlorosilane comprising charging styrene to a reactor; adding an amount of tertiary amine effective for causing formation of β-phenylethylchlorosilane isomer; stirring the styrene-tertiary amine mixture for 15 to 30 minutes; adding platinum metal or platinum metal complex catalyst; stirring the styrene-tertiary amine-catalyst mixture for 15 to 30 minutes; heating the reaction vessel to about 80° C.; adding chlorosilane to the styrene-tertiary amine-catalyst mixture at a rate such that the reactor temperature remains in the range of 80° C. to 100° C.; heating the reaction mixture for about 60 minutes; and stripping at about 100° C. until excess styrene has been removed.

23. The method of claim 22 wherein the tertiary amine is provided as a 1 percent solution in styrene.

24. The method of claim 22 wherein the reaction is carried out under pressure.

25. The method of claim 22 wherein the stripping is carried out under vacuum and a nitrogen sparge.

* * * * *